United States Patent [19]

Hashimoto et al.

[11] Patent Number: 5,354,687
[45] Date of Patent: Oct. 11, 1994

[54] LACTOBACILLUS CASEI (BP-4442)

[75] Inventors: Hideo Hashimoto, Yokohama; Hayami Ito, Himeji, both of Japan

[73] Assignee: Japanese Research & Development Association For New Food Materials, Japan

[21] Appl. No.: 24,087

[22] Filed: Mar. 1, 1993

[30] Foreign Application Priority Data

Feb. 27, 1992 [JP] Japan .................................. 4-075622

[51] Int. Cl.$^5$ .......................... C12N 1/20; C12N 1/00
[52] U.S. Cl. .................................. 435/252.9; 435/856
[58] Field of Search ............................. 435/252.9, 856

[56] References Cited

PUBLICATIONS

Renner et al. (1991) Mutation Research, 262, 239–245.
Fuller (1989) Journal of Applied Bacteriology, 66, 365–378.
Hammes et al. (1994) The Prokaryotes: A Handbook on the Biology of Bacteria: Ecophysiology, Isolation, Identification, Applications. vol. II (Bilous et al Eds.), 1525–94.
ATCC Catalogue of Bacteria and Bacteriophages 17th Ed. 1989, pp. 115–116.
Japanese Laid Open Patent Application No. 228224/1987 (English Abstract attached).
Hosono and Adachi, "Mutagenic and Desmutagenic Factors in Animal Products," *Japanese Journal of Dairy and Food Science*.
Ayebo et al., "Ion Exchange Separation of the Antitumor Component(s) of Yogurt Dialyzate," 1982 J. Dairy Sci 65:2388–2390.
Reddy et al. "Antitumor Activity of Yogurt Components," Journal of Food Protection, vol. 46, No. 1, pp. 8–11, Jan. 1983.
Hosono et al., "Antimutagenic Properties of Lactic Acid Cultured Milk on Chemical and Fecal Mutagens," 1986 J. Dairy Sci 69:2237–2242.

*Primary Examiner*—Irene Marx
*Assistant Examiner*—Jeffrey J. Sevingny
*Attorney, Agent, or Firm*—Wigman, Cohen, Leitner & Myers

[57] ABSTRACT

Described herein is a bacterium having high antimutagenicity against mutagens and belonging to the genus of Lactobacillus. The mutagens may comprise both a base-pair change mutagen and a frameshift mutagen. The bacterium preferably has high intestine reachability and can be *Lactobacillus casei*.

1 Claim, No Drawings

LACTOBACILLUS CASEI (BP-4442)

BACKGROUND OF THE INVENTION

1 Field of the Invention

This invention relates to a novel bacterium belonging to the genus of Lactobacillus, and more specifically to a novel bacterium which belongs to the genus of Lactobacillus, has high antimutagenicity and is advantageously usable in health promoting foods, health care foods and the like.

2 Description of the Related Art

Foods are known to contain numerous mutagens. For example, it is known that 3-amino-1-methyl-5H-pyrido[4,3-b]-indole (hereinafter abbreviated as "Trp-P-2") and the like are contained in scorched parts of meat or fish. A nitroso compound is also known to be formed as a result of food poisoning when certain specific kinds of fish and vegetable are taken together. In addition, growth of a mold on a food is known to result in the formation of aflatoxin or the like as a metabolite. Many of these mutagens have already been found to be carcinogens. From the viewpoint of mutating toxicity, canceration and senescence of human cells are said to have a close relationship with foods to be taken. It is therefore desired to eliminate mutagens from foods.

As methods for eliminating these substances contained in foods, methods making use of an enzyme have heretofore been reported. Among these, as one example in which a lactic acid bacterium is employed, there is known the method disclosed in Japanese Patent Publication No. 228224/1987, in which a peroxidase, thiocyanate ions and/or halogen ions are added to a fermented solution of a lactic acid bacterium, said solution being maintained at 10° C. or lower, whereby a fermented food of the lactic acid bacterium is produced.

Reflecting the ever-increasing concern about health in recent years, there is a tendency toward requiring foods not only to replenish nourishing but also to exhibit a positive health-maintaining function. Foods containing a lactic acid bacterium, such as fermented milk, are also attracting interests as health promoting foods or health care foods. As a matter of fact, it has been reported that a fermented milk has ability to reduce influence of a mutagen contained in foods [Akiyoshi Hosono "Japanese Journal of Dairy and Food Science", 35 (6), A-283 to A-289 (1986)].

In the above report, however, it is not disclosed clearly what component or components in the fermented milk drink act most effectively, especially how antimutagenicity is associated with a lactic acid bacterium itself.

SUMMARY OF THE INVENTION

The present inventors paid attention to such antimutagenicity of lactic acid bacteria as described above and have proceeded with an investigation. As a result, it has been found that lactic acid bacteria include a group of bacteria belonging to the genus of Lactobacillus and having high antimutagenicity against mutagens, leading to the completion of the present invention.

In one aspect of the present invention, there is thus provided a bacterium which has high antimutagenicity against mutagens and belongs to the genus of Lactobacillus.

Although it has not been elucidated how the antimutagenic bacterium according to this invention has high antimutagenicity compared with general Lactobacillus bacteria, the high antimutagenicity is believed to be attributable to a certain interaction which takes place between one or more mutagens and the antimutagenic bacterium.

Since the antimutagenic bacterium according to the present invention has high antigenicity against mutagens, positive health-maintaining effects can be expected from daily intake of foods containing the bacterium, for example, a fermented milk and/or a Lactobacillus beverage in combination with other foods. Further, even in the form of lyophilized liable cells, the antimutagenic bacterium according to the present invention can be applied widely in the food industry and the like.

In particular, use of the antimutagenic bacterium having high intestine reachability permits its existence as flora not only in the pharynx and the mouth but also in the digestive tract. The antimutagenic bacterium according to the present invention is therefore highly expected to eliminate or inhibit mutagens which cause canceration in the digestive tract.

DETAILED DESCRIPTION OF THE INVENTION AND PREFERRED EMBODIMENTS

Bacteria having high antimutagenicity and useful in the practice of the present invention (hereinafter called "antimutagenic bacteria") can be isolated and collected from the nature or various fermented milk, for example, by a screening method to be described below. Incidentally, the term "antimutagenicity" as used herein means any action capable of suppressing and reducing influence which a mutagen gives and includes such an action as inactivating the mutagen itself.

Namely, after separating colonies of a lactic acid bacterium from a sample containing the lactic acid bacterium, for example, from a fermented milk, the colonies are fished and subjected to axenic culture so that a test lactic acid bacterium strain is obtained. The test lactic acid bacterium strain is then prepared to a suitable viable count, for example, to about 2 to $3 \times 10^8$ cells per ml, to which a mutagen, for example, N-methyl-N'-nitro-N-nitrosoguanidine (hereinafter abbreviated as "MNNG"), Trp-P-2, aflatoxin or benzopyrene is added in combination with a mutation testing bacterium, for example, *Salmonella typhimurium* TA100 strain or *Escherichia coli* WP2uvrA. Subsequent to preincubation of the resulting mixture, the preincubate is cultured for a suitable time in a solid medium. Reverse mutant colonies occurred on the mutation testing bacterium are detected. Based on the number of these colonies, the antimutagenic activity of each test lactic acid bacterium is evaluated.

One example of the screening method described above will next be described more specifically. The present inventors developed this specific illustrative method by improving the Ames test which is widely known as a testing method of antimutagenicity. It can quickly screen antimutagenic bacteria.

1. A test sample is sampled in an amount as needed and is diluted and suspended in physiological saline. The suspension is smeared on bromocresol purple plate count agar medium (B.C.P. medium) and allowed to grow there. Representative colonies are fished from the medium and then suspended in physiological saline. The suspension is again smeared on B.C.P. medium and allowed to grow there. These procedures are repeated to isolate the lactic acid bacterium in a pure form.

2. The lactic acid so obtained is cultured at 30° C. or 37° C. for about 17 hours in a liquid medium (MRS). The culture is subjected to filtration, centrifugation or the like, whereby only cells are collected. The cells are washed with a buffer to adjust the viable count to 2 to $3 \times 10^8$ cells per ml.

3. A 0.1 ml portion of the lactic acid bacterium solution obtained above in step 2 is placed in a sterilized test tube, followed by the addition of a mutagen in an amount as needed. Depending on the mutagen, S9-mix is added further.

4. The mixture obtained above in step 3 is added with 0.1 ml of a culture of the mutation testing bacterium, *Salmonella typhimurium* TA100 strain. The resulting mixture is shaken at 37° C. for 20 minutes in a constant-temperature shaking culture tank, so that preincubation is effected.

5. A top agar is then added and mixed. The mixture so prepared is poured onto a minimum glucose medium and is spread evenly.

6. The light is shielded and the mutation testing bacterium is cultured at 37° C. for 48 hours or longer.

7. Colonies formed by reverse mutation are counted.

Upon conducting the above test, it is necessary to provide a positive control containing the mutagen, S9-mix and the mutation testing bacterium, a standard control similar to the positive control except for the omission of the mutagen, and a further control containing only a test lactic acid bacterium.

To calculate the antimutagenicity rate from the above results, the following formula can be followed:

Antimutagenicity rate $= [(B-A)/(B-C)] \times 100$ where

A: number of colonies of the reverse mutant when the mutagen and the lactic acid bacterium are added, B: number of colonies of the reverse mutant when only the mutagen is added, and C: number of colonies of the reverse mutant when only the lactic acid bacterium is added.

By the above method, an antimutagenic bacterium can be isolated and collected. According to the results of tests conducted by the present inventors, it has been found that the existence or absence of antimutagenicity depends considerably on strains even when they are bacteria belonging commonly to the genus of lactobacillus and is not governed by differences in species and that the antimutagenicity of each antimutagenic bacterium varies depending on the mutagen.

The antimutagenicity of each bacterium useful in the practice of the present invention is preferably 40–55% or higher in terms of antimutagenicity rate described above. Further, it is also desired that each bacterium has such antimutagenicity against both base-pair change mutagens and frameshift mutagens.

Each antimutagenic bacterium useful in the practice of the present invention is selected from bacteria belonging to the genus of Lactobacillus. Of these, selection of a Lactobacillus bacterium having resistance to digestive enzymes and bile acid led by human gastric juice, that is having so-called intestine reachability, for example, *Lactobacillus casei* or *Lactobacillus acidophilus*, especially *Lactobacillus casei* is preferred.

Each Lactobacillus bacterium having intestine reachability is considered to become flora in the intestinal tract and hence to effectively protect the intestinal tissue from mutagens which are said to exist abundantly in the intestinal tract, so that such a Lactobacillus bacterium is more preferable than other Lactobacillus bacteria.

The followings are taxonominal characteristics of *Lactobacillus casei* LA2 strain which the present inventors selected as a representative example of bacteria useful in the practice of the present invention from lactic acid bacteria in various fermented foods obtained in Japan or abroad and over 150 strains of eleven species of lactic acid bacteria stored at various depositary authorities.

(Taxonominal characteristics)

Culture medium: Skim milk. When cultured at 37° C., the lactic acid acidity reached 0.8% in 17 hours.

Shape: Rod of 0.5 to $1.0 \times 5$ to 10 μm.

Spores: None.

Physiological properties:

Lactic acid fermentation: Homogeneous.

Gram stain: Positive.

Catalase: None.

Growth temperature: 15°–45° C.

Optimal growth temperature: 38° C.

Growth on media:

Meat extract agar plate medium:

Good growth is shown in 37–48 hours (white colonies).

Meat extract liquid medium:

Growth is observed.

Litmus milk:

Coagulation (acidic).

Assimilation of saccharides:

| Saccharide | Standard *casei** | *Casei* LA2 |
| --- | --- | --- |
| Amygdalin | + | + |
| Arabinose | − | − |
| Cellobiose | + | + |
| Esculin | + | + |
| Fructose | + | + |
| Galactose | + | + |
| Glucose | + | + |
| Gluconate | + | − |
| Lactose | + | + |
| Maltose | + | + |
| Mannitol | + | + |
| Mannose | + | + |
| Melezitose | + | + |
| Melibiose | − | − |
| Raffinose | − | − |
| Rhamnose | + | + |
| Ribose | + | + |
| Salicin | + | + |
| Sorbitol | + | + |
| Sucrose | ± | + |
| Trehalose | + | + |
| Xylose | − | − |

*Standard *casei*: *Lactobacillus casei* JCM 1136.

From the above results, *Lactobacillus casei* LA2 strain has been confirmed to be a species of *Lactobacillus casei*. It however has a property not observed on casei bacteria generally used in the dairy industry, that is, high antimutagenicity, so that the present inventors determined it as a new strain and deposited the same on Feb. 10, 1992 with Fermentation Research Institute, Agency of Industrial Science and Technology (FERM P-12756).

Further, the above-described testing method developed by the present inventors can be used in a variety of fields because it makes it possible to efficiently screen not only Lactobacillus bacteria but also other bacteria having antimutagenicity.

The present invention will next be described in further detail by the following examples. It is however to be borne in mind that the present invention is by no means limited to or by the examples.

EXAMPLE 1

Screening of antimutagenic lactic acid bacteria:

Specimens such as fermented foods collected at various places around the world were each sampled in an amount as needed. After the specimen was diluted and suspended in physiological saline, the suspension was smeared and cultured on B.C.P. medium. A representative lactic acid bacterium was fished from colonies which had grown on the medium. The lactic acid bacterium was again suspended in physiological saline and the resulting suspension was smeared and cultured on B.C.P. medium. Those procedures were repeated to isolate the lactic acid bacterium in a pure form. The thus-obtained strain of lactic acid bacterium was cultured at 30° C. or 37° C. for 17 hours in a liquid medium (MRS medium). The culture so obtained was centrifuged at 3,000 G to collect cells. Those cells were then washed with phosphate buffer (pH 7.4). Those procedures were repeated thrice, followed by the adjustment of its viable count with the same buffer to 2 to $3 \times 10^8$ cells per ml.

A 0.1 ml portion of the solution of the lactic acid bacterium strain so prepared was placed in a sterilized test tube, followed by the addition of 5 $\mu$g of MNNG as a representative base-pair change mutagen and by the further addition of *Salmonella typhimurium* TA100 strain. The resultant mixture was shaken at 37° C. for 20 minutes in a constant-temperature water tank so that preincubation was effected. Top agar was then added and mixed, and the mixture so prepared was poured on a minimum glucose medium and then spread evenly. While the medium was shielded from the light, culture was conducted at 37° C. for 48 hours. Histidine non-requiring colonies formed by reverse mutation of the *Salmonella typhimurium* were then counted, whereby the antimutagenicity rate was calculated. From Lactobacillus bacteria fished by the present inventors from the fermented foods and also from over 150 strains of 11 species of lactic acid bacteria stored at various depositary authorities, 9 strains were obtained in total as strains having an antimutagenicity rate of at least 55% against MNNG.

Additional tests were also conducted in a similar manner to the above-described tests except for the use of S9-mix and, as a mutagen, Trp-P-2, a representative frameshift mutagen, whereby 8 strains were obtained in total as strains having an antimutagenicity rate of at least 55% against Trp-P-2.

Of these, two strains which had been screened commonly in both the tests were chosen as antimutagenic bacteria and named "*Lactobacillus casei* LA2 strain" and "*Lactobacillus casei* 1136 strain", respectively. The former is excellent antimutagenicity because its antimutagenicity rates against MNNG and Trp-P-2 are 72% and 77%, respectively.

EXAMPLE 2

Measurement of antimutagenicity against aflatoxin $B_1$:

With respect to *Lactobacillus casei* LA2 strain and *Lactobacillus casei* 1136 strain obtained in Example 1, their antimutagenicity rates against aflatoxin $B_1$ were measured following the method of Example 1. As a result, the antimutagenicity rates of *Lactobacillus casei* LA2 strain and *Lactobacillus casei* 1136 strain were found to be 73.9% and 70.4%, respectively.

EXAMPLE 3

Measurement of antimutagenicity against benzopyrene

In a similar manner to Example 2, the antimutagenicity of *Lactobacillus casei* LA2 strain and *Lactobacillus casei* 1136 strain against benzopyrene was measured. As a result, the antimutagenicity rates of *Lactobacillus casei* LA2 strain and *Lactobacillus casei* 1136 strain were found to be 79.1% and 77.2%, respectively.

EXAMPLE 4

Production of fermented milk drink:

Fresh milk (1 l) was heated at 95° C. for 10 minutes to effect pasteurization. It was cooled down to 37° C. followed by the addition of 3% of *Lactobacillus casei* LA2 strain, which had been cultured in pasteurized skim milk, as a starter. The resulting mixture was cultured at 38° C. for 8 hours so that a fermented milk was produced. Its flavor was substantially the same as a fermented drink produced using a general strain of *Lactobacillus casei*, so that the usefulness of *Lactobacillus casei* LA2 strain in the production of a fermented milk has been confirmed.

We claim:

1. A biologically pure culture of *Lactobacillus casei* (BP4442).

* * * * *